United States Patent
Joo et al.

(12) 
(10) Patent No.: US 6,245,943 B1
(45) Date of Patent: Jun. 12, 2001

(54) METHOD OF PREPARING P-PHENYLENEDIAMINE

(75) Inventors: Young J. Joo; Jin Eok Kim; Jeong Im Won, all of Taejon (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 09/639,507

(22) Filed: Aug. 16, 2000

(30) Foreign Application Priority Data

Jul. 7, 2000 (KR) .................................................. 00-38764

(51) Int. Cl.$^7$ .................................................. C07C 209/00
(52) U.S. Cl. .......................... 564/423; 564/414; 564/420; 564/422
(58) Field of Search .................................... 564/414, 420, 564/422, 423

(56) References Cited

U.S. PATENT DOCUMENTS

| | | | |
|---|---|---|---|
| 4,020,052 | 4/1977 | Detrick | 260/140 R |
| 4,279,815 | 7/1981 | Herkes | 260/205 |
| 5,380,946 | 1/1995 | Stern et al. | 564/124 |
| 5,436,371 | 7/1995 | Stern et al. | 564/124 |
| 6,156,932 | * 12/2000 | Joo et al. | |

FOREIGN PATENT DOCUMENTS

WO 932447 12/1993 (WO) .............................. C07C/06/80

* cited by examiner

*Primary Examiner*—Samuel Barts
(74) *Attorney, Agent, or Firm*—Davidson, Davidson & Kappel, LLC

(57) ABSTRACT

A disclosed method of preparing p-phenylenediamine includes the steps of: reacting urea and nitrobenzene with a base in the presence of a polar solvent to yield 4-nitrosoaniline and 4-nitroaniline; and subsequently, diluting the resulting mixed solution in an alcohol and performing hydrogenation using a catalyst, thereby providing highly pure p-phenylenediamine destitute of an ortho- or meta-isomer as a byproduct. The method has some advantages in that: the process is simplified in such a manner that the hydrogenation is performed in the presence of the hydrogenation catalyst in a single reactor (i.e., one pot) without a need of isolating 4-nitrosoaniline or purifying the product; inexpensive urea and an alkali base are used to reduce the production cost; and 4-nitrosoaniline is formed as an intermediate to yield p-phenylenediamine with a high selectivity, thereby requiring no purification process after isolation of the product.

6 Claims, No Drawings

METHOD OF PREPARING P-PHENYLENEDIAMINE

TECHNICAL FIELD

The present invention generally relates to a method of preparing pphenylenediamine and, more particularly, to a novel method of preparing highly pure pphenylenediamine, which involves reacting urea and nitrobenzene with a base in the presence of a polar organic solvent to yield 4-nitrosoaniline and 4-nitroaniline and then performing hydrogenation using a catalyst.

BACKGROUND ART p-phenylenediamine is a compound of various applications such as cosmetic, antioxidant, fuel additive and dyestuff and, more particularly, a useful compound as a base material of a highly resilient and heat-resistant material (e.g., aramide fiber) and a raw material of polyurethane, p-phenylenediisocyanate.

Conventionally, there have been used two commercialized methods for preparing p-phenylenediamine of such a wide use range. The first method involves reacting chlorobenzene with nitric acid and reacting the resulting product, p-nitrochlorobenzene with ammonia to yield 4-nitroaniline, followed by hydrogenation of 4-nitroaniline to produce p-phenylenediamine. The second method involves diazotation of aniline using nitrogen oxide, reaction with an excess of aniline to form 1,3-diphenyltriazene, and rearragement of 1,3-diphenyltriazene to 4-aminoazobenzene and hydrogenation of 4-aminoazobenzene to yield p-phenylenediamine and aniline.

The first method is most widely used and yields isomers of nitrochlorobenzene, i.e., ortho- and para-forms at a ratio of 65:35 through nitration of chlorobenzene in order to form an intermediate, 4-nitroaniline. At this stage, however, the final product is not isolated as pure p-phenylenediamine but stained with a small amount of isomers. Thus this method is normally used to prepare p-phenylenediamine of low purity or dyes. Another disadvantage of the method is to dispose of a large quantity of wastewater due to the chlorine-containing materials used.

The second method solves the problem related to production of an isomer such as ortho-form. Specifically, the method involves diazotating aniline with nitrogen oxide and reacting the resulting diazo-compound with an excess of aniline to yield 1,3-diphenyltriazene, which is then subjected to rearrangement and hydrogenation reaction to provide aniline such as p-phenylenediamine (See. U.S. Pat. Nos. 4,020,052 and 4,279,815). This method may produce a relatively pure p-phenylenediamine but requires complicated multi-stage reactions.

Recently, a method of preparing 4-nitroaniline in two steps has been developed (See. J. Am. Chem. Soc., 1992, 114(23); J. Org. Chem., 1993, 58, 6883–6888; U.S. Pat. Nos. 5,436,371 and 5,380,946; and WO 93/24447). The method includes the steps of performing the NASH (Nucleophilic Aromatic Substitution of Hydrogen) to synthesize an intermediate, N-(4-nitrophenyl)benzamide through the reaction of benzamide and nitrobenzene with an organic base, and adding water (or ammonia) to the intermediate to decompose the intermediate into 4-nitroaniline and benzoic acid (or benzamide). This method provides 4-nitroaniline in the para-form with a relatively high selectivity and may be used to prepare highly pure p-phenylenediamine through hydrogenation. However, the method produces 4-nitroaniline in two stages with a low yield due to the water content in the reaction mixture. Furthermore, it requires a need of using a relatively high-cost material, TMA(OH) as an organic base.

DISCLOSURE OF INVENTION

In an attempt to solve the problems of the NASH-based method, the inventors have contrived a method of selectively preparing 4-nitrosoaniline under a simple condition relative to the related arts by reacting nitrobenzene with urea instead of benzamide in the presence of an alkali base.

It is therefore an object of the present invention to provide a novel method of preparing p-phenylenediamine destitute of ortho- or meta-phenylenediamine as an isomeric byproduct through a hydrogenation using Pd/C or Pt/C as a catalyst in a single reactor (i.e., one pot) without a need of isolation or purification.

It is another object of the present invention to provide a novel method of preparing p-phenylenediamine, in which inexpensive urea and an alkali base are used to reduce the production cost and 4-nitrosoaniline is formed as an intermediate to yield p-phenylenediamine with a high selectivity, thereby requiring no purification process after isolation of the product.

To achieve the above object, there is provided a method of preparing p-phenylenediamine including the steps of: reacting urea and nitrobenzene with a base in the presence of a polar solvent to yield 4-nitrosoaniline and 4-nitroaniline; and subsequently, diluting the resulting mixed solution in an alcohol and performing hydrogenation using a catalyst.

BEST MODE FOR CARRYING OUT THE INVENTION

The present invention will now be described in detail as follows.

The present invention is directed to a novel method of preparing highly pure p-phenylenediamine by reacting urea and nitrobenzene with a base in the presence of a polar organic solvent such as dimethyl sulfoxide to yield 4-nitrosoaniline and 4-nitroaniline and performing hydrogenation using a Pd/C or Pt/C catalyst.

In the preparation of p-phenylenediamine according to the present invention, urea and nitrobenzene are first reacted with a base in the presence of a polar organic solvent such as dimethyl sulfoxide to yield 4-nitrosoaniline and 4-nitroaniline.

Examples of the base as used herein may include a relatively inexpensive organic base such as alkali metals and alkali earth metals. And, examples of the solvent as used herein may include a polar solvent such as dimethyl sulfoxide, dimethyl formamide, N-methyl pyrrolidinone, etc., which is chosen in consideration of the solubility of the organic base.

The proportion of 4-nitrosoaniline or 4-nitroaniline to be yielded is controllable by regulating the ratio of urea to nitrobenzene. That is, an increase in the ratio of urea to nitrobenzene raises the yield proportion of 4-nitrosoaniline. A high proportion of nitrobenzene to urea leads to a large yield of 4-nitroaniline so as to make the secondary product of 4-nitroaniline, 4,4'-dinitrodiphenylamine detectable. Preferably, the ratio of urea to nitrobenzene is in the range of 1 to 10 equivalents.

Subsequently, the primary products of urea and nitrobenzene, i.e., 4-nitrosoaniline and 4-nitroaniline are hydrogenated with a Pd/C or Pt/C catalyst to yield highly pure p-phenylenediamine.

It is desirable that an alcohol such as ethanol or isopropanol is added to dilute the mixed solution of 4-nitrosoaniline and 4-nitroaniline prior to hydrogenation and that the added amount of the alcohol is 50 to 500 parts by weight based on 100 parts by weight of the polar solvent. The reaction will not occur unless the solvent is diluted with alcohol prior to hydrogenation.

The amount of the hydrogenation catalyst such as Pd/C or Pt/C is preferably in the range of 0.1 to 10 parts by weight based on 100 parts by weight of 4-nitrosoaniline and 4-nitroaniline in total.

Preferably, the reaction temperature is in the range from the room temperature to 200° C. The reaction temperature below the range inactivates the reaction and the lower reaction temperature retards the reaction. Contrarily, the higher reaction temperature causes an increase in the reaction velocity.

Preferably, the hydrogen pressure is in the range of 50 to 500 psi. An increase in the hydrogen pressure also raises the reaction velocity.

The present invention is preferable in preparing highly pure p-phenylenediamnine without an isomeric byproduct by hydrogenation, because it yields 4-nitrosoaniline and 4-nitroaniline as intermediates without an ortho-compound as a byproduct, such as 2-nitrosoaniline or 2-nitroaniline from inexpensive urea and nitrobenzene.

Advantageously, the present invention also provides a preparation of highly pure p-phenylenediamine through hydrogenation in a single reactor (i.e., on e pot) neither requiring a separate reactor for providing an anhydrous condition nor an isolation process after production of 4-nitrosoaniline, because the water content does not affect the reaction significantly.

For an understanding of the present invention, a method of preparing p-phenylenediamine will be exemplified by way of the following examples, in which the products of the present invention were analyzed qualitatively by the NMR (nuclear Magnetic Resonance) spectrum and the GC-MSD) (Gas Chromatographic and Mass Spectroscopic Detector) and quantitatively by the GC and the HPLC (High Performance Liquid Chromatography).

A quantitative analysis for all substances was performed by gas chromatography under the conditions as follows:

1) Capillary column: ULTRA2 (Crosslinked 5% Ph-Me Silic one)50 m×0.2 mm×0.33 $\mu$m;
2) Carrier gas: Nitrogen;
3) Head pressure: 20 psi;
4) Oven: 100–280 ° C. (2 min), $\beta$=10° C./min;
5) Detector and temperature: FID (280° C.);
6) Split ratio: 30:1; and
7) Make-up gas flow rate: 38 ml/min.

For a conditioned-weight test of the product, pyrene was used as an internal standard material and the standard calibration involved determining the area ratio for the concentration of the individual substances based on the area of the pyrene. The molar concentration of the individual products was calculated by the calibration-curve method and the yields of 4-nitrosoaniline and 4-nitroaniline were determined based on nitrobenzene.

The present invention will be described below in further detail with reference to the following examples, which illustrate but are not intended to limit the present invention.

Example 1

Urea (120 g, 2 moles), potassium hydroxide (158 g, 2.4 moles), pyrene (6 g) and DMSO (Dimethyl Sulfoxide) (80 g) were added to a one-liter reactor equipped with a condenser and a thermometer. The mixture was stirred under oxygen atmosphere and warmed to 90° C., at which temperature a mixed solution of nitrobenzene (74 g, 0.6 mol) and DMSO (80 g) was added dropwise to the mixture with an adding funnel. It has to be noted that the internal temperature of the reactor should not exceed 90±4° C. The ending point of the reaction was determined by gas chromatography as the time at which nitrobenzene disappears. The reaction time took 1.5 to 2 hours. Thus, based on the total weight of nitrobenzene, 88-mole % of 4-nitrosoaniline and 12-mole % of 4-nitroaniline were obtained, as determined by a quantitative analysis using pyrene as the internal standard material.

The mixed solution was added to a 2-liter pressure reactor and diluted in 300 ml of ethanol, after which a hydrogenation was effected by addition of 3 g of 5% Pd/C catalyst under hydrogen pressure of 120 psi at 90° C.

The product thus obtained was purified by gas chromatography to provide highly pure p-phenylenediamine in 100% yield without a byproduct such as ortho- or meta-phenylenediamine.

Example 2

The same procedures as described in Example 1 were performed with the exception that the hydrogenation was effected by 3% Pt/C catalyst.

The product thus obtained was purified by gas chromatography to provide highly pure p-phenylenediamine in 100% yield.

Industrial Applicability

As described above, the preparation method of the present invention involves reacting urea and nitrobenzene with a base in the presence of a polar organic solvent to yield 4-nitrosoaniline and 4-nitroaniline and performing hydrogenation with a catalyst to provide highly pure p-phenylenediamine without an isomeric byproduct such as ortho- or meta-phenylenediamine, whereby the process is simplified in such a manner that the hydrogenation is performed in the presence of the hydrogenation catalyst in a single reactor (i.e., one pot) without a need of isolating 4-nitrosoaniline or purifying the product. The method is also advantageous in that inexpensive urea and an alkali base are used to reduce the production cost and that 4-nitrosoaniline is formed as an intermediate to yield p-phenylenediamine with a high selectivity, thereby requiring no purification process after isolation of the product.

What is claimed is:

1. A method of preparing p-phenylenediamine comprising the steps of:

reacting urea and nitrobenzene with a base in the presence of a polar solvent to yield 4-nitrosoaniline and 4-nitroaniline; and subsequently, diluting the resulting mixed solution in an alcohol and performing hydrogenation using a catalyst.

2. The method as claimed in claim 1, wherein the hydrogenation catalyst is Pd/C or Pt/C.

3. The method as claimed in claim 1 or 2, wherein the added amount of the hydrogenation catalyst is 0.1 to 10 parts by weight based on 100 parts by weight of 4-nitrosoaniline and 4-nitroaniline in total.

4. The method as claimed in claim 1, wherein the added amount of the alcohol is 50 to 500 parts by weight based on 100 parts by weight of the polar solvent.

5. The method as claimed in claim 1, wherein the reaction temperature for the hydrogenation is the room temperature to 200° C.

6. The method as claimed in claim 1, wherein the hydrogen pressure for the hydrogenation is 50 to 500 psi .

* * * * *